United States Patent
Wilk

(10) Patent No.: US 6,776,754 B1
(45) Date of Patent: *Aug. 17, 2004

(54) METHOD FOR CLOSING OFF LOWER PORTION OF HEART VENTRICLE

(75) Inventor: Peter J. Wilk, New York, NY (US)

(73) Assignee: Wilk Patent Development Corporation, New York, NY (US)

( * ) Notice: Subject to any disclaimer, the term of this patent is extended or adjusted under 35 U.S.C. 154(b) by 644 days.

This patent is subject to a terminal disclaimer.

(21) Appl. No.: 09/678,134

(22) Filed: Oct. 4, 2000

(51) Int. Cl.[7] .................................................. A61F 1/00
(52) U.S. Cl. ......................................... 600/16; 128/898
(58) Field of Search ............................. 600/16, 17, 18, 600/37; 128/898, 897, 899; 606/139, 213

(56) References Cited

U.S. PATENT DOCUMENTS

| | | |
|---|---|---|
| 5,766,216 A | 6/1998 | Gangal et al. |
| 5,800,528 A | 9/1998 | Lederman et al. |
| 5,853,422 A * | 12/1998 | Huebsch et al. ............ 606/213 |
| 5,865,791 A | 2/1999 | Whayne et al. |
| 5,879,366 A * | 3/1999 | Shaw et al. ................. 606/213 |
| 5,928,250 A | 7/1999 | Koike et al. |
| 5,961,440 A | 10/1999 | Schweich, Jr. et al. |
| 6,155,968 A | 12/2000 | Wilk |
| 6,171,329 B1 * | 1/2001 | Shaw et al. ................. 606/213 |
| 6,258,021 B1 * | 7/2001 | Wilk ............................ 600/16 |
| 6,260,552 B1 * | 7/2001 | Mortier et al. .............. 128/898 |
| 6,537,198 B1 * | 3/2003 | Vidlund et al. ............... 600/16 |
| 6,572,529 B2 * | 6/2003 | Wilk ............................ 600/16 |
| 6,616,684 B1 * | 9/2003 | Vidlund et al. ............. 606/213 |
| 6,629,921 B1 * | 10/2003 | Schweich, Jr. et al. ....... 600/16 |
| 2001/0041821 A1 * | 11/2001 | Wilk ............................ 600/16 |
| 2003/0102000 A1 * | 6/2003 | Stevens et al. ............. 128/898 |

* cited by examiner

Primary Examiner—Kathryn Odland
(74) Attorney, Agent, or Firm—R. Neil Sudol; Henry D. Coleman; William J. Sapone

(57) ABSTRACT

A cardiac insert or implant is deployed in a patient's heart so as to reduce ventricular volume, thereby improving cardiac function. The insert or implant may be a compressive device such as a tensile member inserted into the patient's heart, and thereafter operated or deployed to bring opposite walls of a ventricle of the patient's heart into at least approximate contact with one another to thereby constrict and close off a lower portion of that ventricle. The compressive device or tensile member is insertable into the patient heart via a catheter threaded through the patient's vascular system and into the patient's heart.

21 Claims, 2 Drawing Sheets

METHOD FOR CLOSING OFF LOWER PORTION OF HEART VENTRICLE

BACKGROUND OF THE INVENTION

This invention relates to a method and device for improving cardiac function, particularly where there is congestive heart failure.

Congestive heart failure occurs, inter alia, where there has been a heart attack or an infection. In either case, the pumping action of the heart is impaired. In another malfunction, left ventricular hypertrophy, the myocardium of the left ventricle becomes thickened to the point of interfering with effective heart contraction.

A surgical procedure for treating congestive heart failure, developed by a doctor in Brazil, involves removing a triangular portion of a patient's heart. In this operation, approximately one-third of the patient's left ventricular muscle is removed. The result is that the smaller heart pumps more efficiently.

This new technique of course requires open heart surgery, with its attendant expense and extended convalescence.

OBJECTS OF THE INVENTION

An object of the present invention is to provide a surgical method for treating congestive heart failure.

A further object of the present invention is to provide such a surgical method which is less expensive than the above-described surgical technique.

It is another object of the present invention to provide a surgical method for treating congestive heart failure which may be implemented through minimally invasive procedures.

An additional object of the present invention is to provide a device for implementing such a surgical method.

These and other objects of the present invention will be apparent from the drawings and descriptions herein.

SUMMARY OF THE INVENTION

The present invention is directed to the disposition of a cardiac insert or implant in a patient's heart so as to reduce ventricular volume, thereby improving cardiac function.

More specifically, pursuant to one embodiment of the present invention, a method for improving cardiac function comprises inserting a compressive device into a patient in a region including the patient's heart, and thereafter operating the compressive device to bring opposite walls of a ventricle of the patient's heart into at least approximate contact with one another to thereby constrict and close off a lower portion of that ventricle. Pursuant to a feature of the present invention, the compressive device is operated to effectively close off only the lower portion of only the one ventricle. Preferably, the one ventricle is the left ventricle of the patient's heart. The left ventricle remains a single cell chamber of smaller volume.

In a more particular implementation of the present invention, the compressive device is inserted through a trocar sleeve or cannula which extends through a chest wall of the patient. In another particular implementation, the compressive device includes a tensile member which is inserted or introduced into the patient through a catheter with a leading end portion guided to a region of the patient's heart. More particularly, a leading end portion of the catheter is inserted into the patient's heart, the tensile member being ejected from the leading end portion of the catheter into cardiac tissues. Where the leading end portion of the catheter is inserted into the right ventricle, the tensile member is ejected through the septum of the patient's heart and the left ventricle and into a myocardial wall of the heart. Where the leading end portion of the catheter is inserted into the left ventricle, the tensile member includes a first segment ejected into or through the septum of the patient's heart and a second segment ejected through or into the myocardial wall of the left ventricle. In either case, operating of the compressive device includes exerting a tension force on the tensile member to draw the septum and the myocardial wall together. In the latter case, the two segments of the tensile member are twisted about one another to draw the septum and the myocardial wall towards one another.

Where the compressive device is a tensile member such as a wire or a suture (made of metal or polymeric material), it may be formed with one or more barbs, particularly at an end, for anchoring the tensile member in the cardiac tissues.

Where the compressive device is inserted through a trocar sleeve or cannula, the compressive device may also take the form of a tensile member such as a wire guided to a predetermined location on the myocardium of the left ventricle by a catheter inserted into a pericardial space about the patient's heart through the trocar sleeve or cannula. The operating of the compressive device includes ejecting the tensile member from the leading end portion of the catheter through a myocardial wall, a left ventricle of the patient's heart and a septum of the heart. The operating of the compressive device further includes exerting a tension force on the tensile member to draw the septum and the myocardial wall of the left ventricle together.

The compressive device, a tensile member in particular embodiments of the present invention, serves to reduce the volume of the left ventricle and only the left ventricle of the patient's heart. The application of the compressive device thus serves to correct certain conditions of the patient's heart in which the pumping capacity of the left ventricle has been reduced. The reduction in the volume of the left ventricle results in a higher blood pressure and thus a more effective transmission of blood especially to peripheral tissues of the patient.

The method of the invention contemplates an anchoring of one end of the tensile compressive member to a septum of the patient's heart and an opposite end of the tensile compressive member to a myocardial sidewall of the left ventricle. The anchoring of the tensile compressive member may be implemented by placing a flanged or barbed element of the tensile member in contact with heart tissues. The barbed element may be embedded inside myocardial tissues or caught in an external surface of the myocardium or septum.

In some embodiments of the present invention, the compressive member may take the form of an elongate tack ejected from a tubular member such a catheter or trocar sleeve or cannula.

It is apparent, therefore, that the present invention is directed in part to a method for reducing ventricular volume, wherein a catheter is inserted into a ventricle of a patient's heart, a cardiac insert or implant is deployed from a leading end portion of the catheter, and the cardiac insert or implant is disposed in the patient's heart to reduce the volume of only a left ventricle of the patient's heart. It is contemplated that the cardiac insert or implant takes the form of a tensile member such as a wire which is attached to the patient's heart. However, other forms of inserts or implants may be effective to reduce ventricular volume.

A surgical method in accordance with the present invention treats congestive heart failure. The method may be performed thoracoscopically which is less expensive and less traumatic to the patient than an open-heart surgical technique. The minimally invasive, intravascularly implemented procedure is even less expensive and less traumatic to the patient. The method of the invention is simple and reliable.

DESCRIPTION OF THE PREFERRED EMBODIMENTS

Figure 1A:
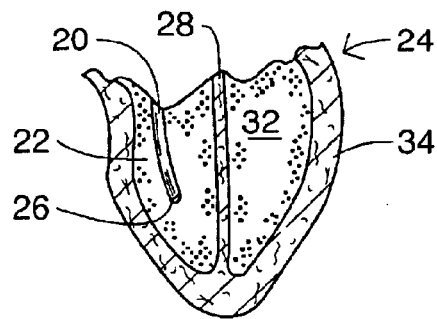
FIGS. 1A through 1D are partial schematic cross-sectional views of a human heart, showing successive steps in a method for reducing ventricular volume, pursuant to the present invention.

As illustrated in FIG. 1A, a method for reducing ventricular volume to improve cardiac functioning includes a step of inserting a distal or leading end portion of a catheter 20 through the vascular system of a patient, and particularly through the vena cava, into the right ventricle 22 of the patient's heart 24. The deployment of catheter 20 is carried out according to procedures that are well known in the art. For example, the catheter 20 may be introduced over a guide wire (not shown) which has been previously threaded through the venous system to the right ventricle 22.

Figure 1B:
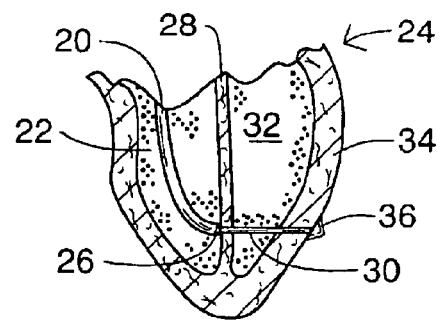

After the distal end portion of catheter 20 has been inserted through the right auricle (not shown) into the right ventricle 22, the catheter is manipulated to place a leading end or tip 26 of catheter 20 into engagement with a lower part of a septum 28 of the patient's heart 24, as shown in FIG. 1B. A compressive cardiac implant or insert in the form of a tensile member 30 such as a wire or a stiff suture is then forcibly ejected from the catheter 20 through septum 28, a lower part of the patient's left ventricle 32, and a generally left wall or myocardium region 34 of the patient's heart 24.

As further illustrated in FIG. 1B, tensile member 30 is formed at a leading end with an anchor 36 in the form of a barb or flange. Anchor 36 has a structure which permits movement of the anchor in one direction through cardiac tissues and prohibits movement of the anchor in the opposite direction through the tissue. For instance, anchor 36 may be hinged to the leading end of tensile member 30 and formed with a stop for arresting rotational motion beyond a predetermined orientation relative to tensile member 20. Prior to the ejection of tensile member 30 from catheter 20, anchor 36 is disposed in a collapsed configuration inside catheter 20. Anchor 36 essentially maintains this collapsed configuration during the ejection process.

Figure 1C:
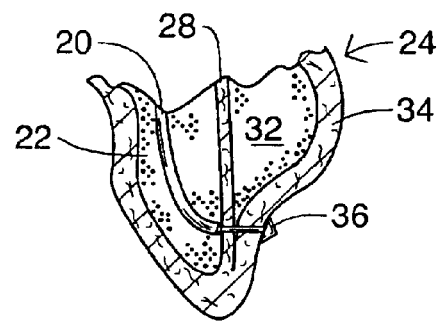

After anchor 36 has passed through heart wall 34, a retraction force is applied to tensile member 30 tending to draw the tensile member back in the catheter 20. As shown in FIG. 1C, this action results in the planting of anchor 36 along the outer side of wall 34 and a drawing together of the lower parts of septum 28 and wall region 34. Septum 28 and heart wall 34 are thus brought into at least approximate contact with one another to effectively close off a lower or apical portion of heart 24, as illustrated in FIG. 1C.

Figure 1D:
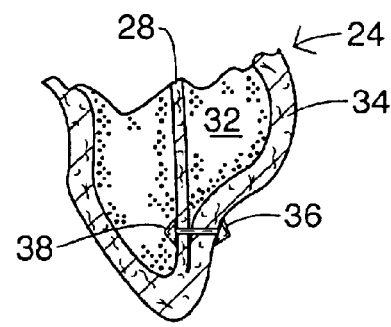

After the limited retraction of tensile member 30 and the consequent closure of the lower or apical portion of heart 24, tensile member 30 is provided with a second anchor 38, as shown in FIG. 1D, and severed on a side of septum 28 inside right ventricle 22. Anchor 38 may be similar in structure to anchor 36 (but oppositely biased;) and permanently attached thereto. In that case, tensile member 30 with anchors 36 and 38 is preselected, prior to insertion in catheter 20, to match the particular heart 24 and deployment location. More specifically, tensile member 30 and anchors 36 and 38 together define a preformed compressive cardiac implant having an interanchor spacing equal to the combined thickness of septum 28 and heart wall 34 at the intended point of deployment of the cardiac implant. The thicknesses of septum 28 and heart wall 34 may be premeasured by a CAT scan or magnetic resonance imaging or through radiographic investigation. Anchor 38 is held in a collapsed configuration by a sleeve (not shown) inside catheter 20, thus enabling a relative motion of anchor 38 in a distal direction (relative to the operator or surgeon) during an implantation operation.

In an alternative structure and method of deployment, anchor 38 is permanently fixed to tensile member 30 only after the ejection of tensile member 30 through septum 28, left ventricle 32, and heart wall 34. Prior to the ejection operation, anchor 38 is housed inside catheter 30 and surrounds tensile member 30. After ejection of tensile member 30, anchor 38 is pushed by an ancillary tubular member (not shown) into contact with the right-ventricle side of septum 28. Anchor 38 is then secured to tensile member 30 by any suitable means. For instance, where tensile member 30 and anchor 38 are made of thermosetting resin or polymeric material, a piezoelectric crystal may be inserted into right ventricle 22 through catheter 20 to ultrasonically weld anchor 38 to tensile member 30. Alternatively, tensile member 30 may be formed with a series of spaced beads and anchor 38 made of an elastic bio-compatible material, so that anchor 38 may be pushed over one or more of the beads and locked to tensile member in a snap-lock fit.

The severing of tensile member 30 on a side of anchor 38 opposite septum 28 is effectuated by any suitable means. A cutting device (not shown) may be inserted into right ventricle 22 and subsequently removed therefrom via catheter 20. Possible kinds of cutting devices for this application have jaws (not shown) or an ultrasonically actuated blade (not shown). Alternatively, catheter 20 might be rotated about its longitudinal axis to effectuate a twisting separation of tensile member 30.

Figure 2A:
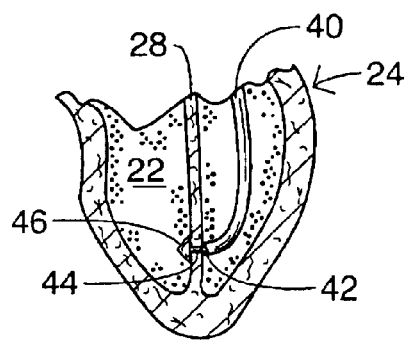
FIGS. 2A through 2F are partial schematic cross-sectional views of a human heart, showing successive steps in another method for reducing ventricular volume, pursuant to the present invention.

As illustrated in FIG. 2A, another method for reducing ventricular volume to improve cardiac functioning of the patient's heart 24 includes a step of inserting a distal or leading end portion of a catheter 40 through the vascular system of the patient, and particularly through the aorta (not shown), into the left ventricle 32 of the heart 24. Again, the particulars of deploying deployment catheter 40 are well known in the art.

Figure 2B:
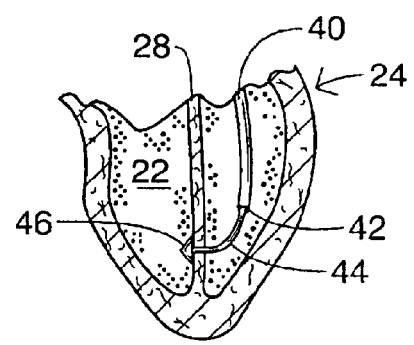

After the distal end portion of catheter 40 has been inserted through the left auricle (not shown) into the left ventricle 32, the catheter is manipulated to place a leading end or tip 42 of catheter 40 into engagement with a lower part of a septum 28 of the patient's heart 24, as shown in FIG. 2A. A compressive cardiac implant or insert segment in the form of a tensile member or wire 44 is then forcibly ejected from the catheter 40 through septum 28, as depicted in FIG. 2B. Tensile member 44 is formed at a leading end with an anchor 46 in the form of a barb or flange. As discussed above with reference to anchor 36, anchor 46 has a structure which permits movement of the anchor in one direction through cardiac tissue and prohibits movement of the anchor in the opposite direction through the tissue. Again, anchor 46 may be hinged to the leading end of tensile member 44 and formed with a stop for arresting rotational motion beyond a predetermined orientation relative to tensile member 44. Prior to the ejection of tensile member 44 from catheter 40, anchor 46 is disposed in a collapsed configuration inside catheter 40. Anchor 46 essentially maintains this collapsed configuration during the ejection process.

Figure 2C:
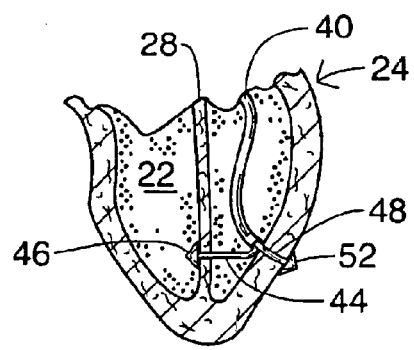

After the piercing of septum 28 by tensile member 44, catheter 40 is withdrawn slightly, as shown in FIG. 2B. Then, catheter 40 is manipulated to place end or tip 42 into engagement with a lower part of heart wall 34, as shown in FIG. 2C. A second compressive cardiac implant or insert segment in the form of a tensile member or wire. 48 is then forcibly ejected from the catheter 40 through heart wall 34, as depicted in FIG. 2C. Tensile member 48 is also formed at a leading end with an anchor 50 in the form of a barb or flange.

Figure 2D:
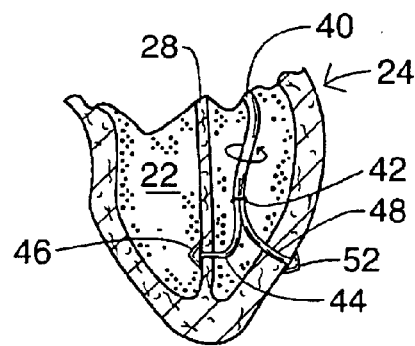
Figure 2E:
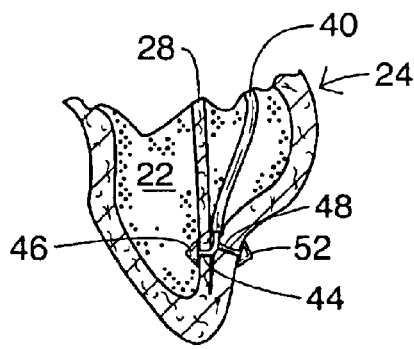
Figure 2F:
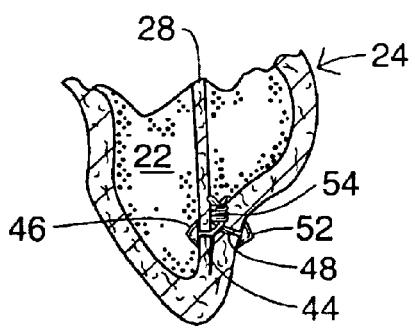

After the piercing of heart wall 34 by tensile member 48, catheter 40 is again pulled back slightly to a position depicted in FIG. 2D. At that juncture, catheter 40 is turned about its longitudinal axis, as indicated by an arrow 52, to twist tensile members or wire segments 44 and 48. Catheter 40 may be provided at its leading end with a cross-bar (not shown) to facilitate the twisting of tensile members or wire segments 44 and 48 about one another, tensile members or wire segments 44 and 48 extending on opposite sides of the cross-bar. The twisting of tensile members or wire segments 44 and 48 draws septum 28 and heart wall 34 together, as shown in FIG. 2E. Eventually, the twisting results in severing of tensile members or wire segments 44 and 48 so that they are joined to one another by a twist knot 54.

Figure 3:
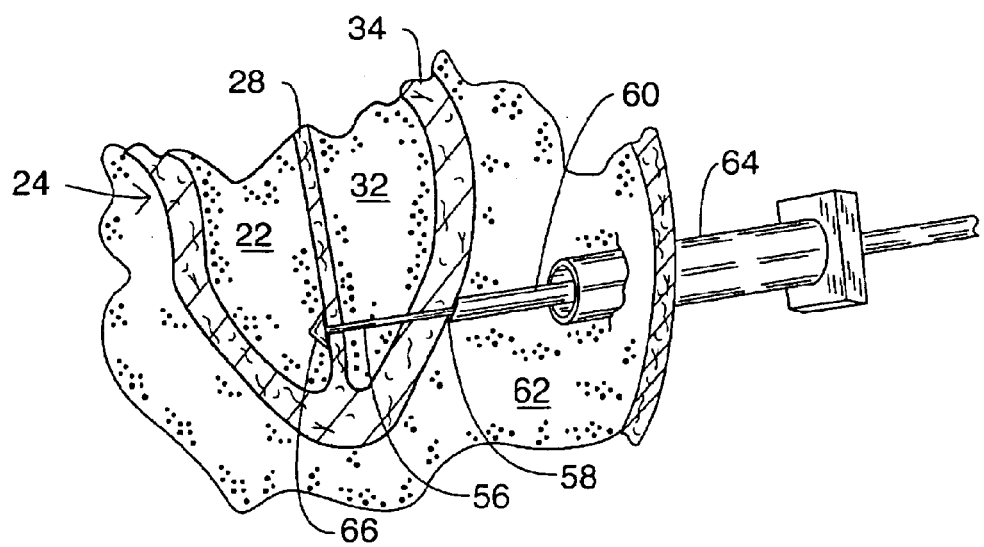
FIG. 3 is a partial schematic cross-sectional views of a human heart, showing a step in yet another method for reducing ventricular volume, pursuant to the present invention.

As shown in FIG. 3, a compressive cardiac implant of insert 56 in the form of a tack is ejected from a free end 58 of a tubular applicator 60 through heart wall 34, left ventricle 32, and septum 28. Applicator 60 is inserted into an intrapericardial space 62 through a thoracoscopic cannula or trocar sleeve 64. Tack 56 is formed at a leading end with an anchor 66 in the form of a barb or flange. Anchor 66 has a structure which permits movement of the anchor in one direction through cardiac tissues and prohibits movement of the anchor in the opposite direction through the tissue.

After the ejection of tack 56 through ventricle 32, a tensile force is placed on tack 56 to draw the tack in a reverse direction and thereby compress the lower portion or apex of ventricle 32 between anchor 66 and the leading end of tubular applicator 60. After the limited retraction of tack 56 and the consequent closure of the lower or apical portion of heart 24, tack 56 is provided with a second anchor (not shown) and severed on a side of heart wall 34 inside the intrapericardial space 62. Where this second, closure, anchor is in the form of a resilient collar and where tack 56 is provided with a series of beads (not shown), the collar may be forced over the beads in seriatim to provide a proper clamping force on the cardiac tissues at the lower end or apex of ventricle 32, thereby bringing septum 28 and heart wall 34 into close proximity (if not actual contact) with one another and thus substantially closing the apical portion of ventricle 32.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A method for improving cardiac function, comprising: inserting a compressive device into a patient in a region including the patient's heart; and
after the inserting of said compressive device into the patient, operating said compressive device to bring opposite walls of only one ventricle of the patient's heart into contact with one another to thereby constrict and close off a lower portion of said one ventricle of the patient's heart.

2. The method defined in claim 1 wherein the operating of said compressive device includes applying said compressive device to close off only said lower portion of said one ventricle of the patient's heart.

3. The method defined in claim 2 wherein said one ventricle is the left ventricle of the patient's heart.

4. The method defined in claim 1 wherein the inserting of said compressive device includes inserting said compressive device through a trocar sleeve or cannula.

5. The method defined in claim 4 wherein said compressive device includes a tensile member, the inserting of said tensile member including introducing said tensile member through a catheter.

6. The method defined in claim 5 wherein the introducing of said tensile member includes passing a leading end portion of said catheter into a pericardial space about the patient's heart, the operating of said compressive device including ejecting said tensile member from said leading end portion of said catheter through a myocardial wall, a left ventricle of the patient's heart and a septum of the patient's heart, the operating of said compressive device further including exerting a tension force on said tensile member to draw the septum and the myocardial wall of said left ventricle together.

7. The method defined in claim 1 wherein said compressive device includes a tensile member, the inserting of said tensile member including introducing said tensile member through a catheter.

8. The method defined in claim 7 wherein the introducing of said tensile member includes passing a leading end portion of said catheter into a right ventricle of the patient's heart, the operating of said compressive device including ejecting said tensile member from said leading end portion of said catheter through a septum and a left ventricle and a myocardial wall of the patient's heart, the operating of said compressive device further including exerting a tension force on said tensile member to draw said septum and said myocardial wall together.

9. The method defined in claim 7 wherein said tensile member includes a first segment and a second segment, the introducing of said tensile member includes passing a leading end portion of said catheter into a left ventricle of the patient's heart, the operating of said compressive device including ejecting said first segment from said leading end portion of said catheter through a septum of the patient's heart and additionally including ejecting said second segment through an outer wall of said left ventricle, the operating of said compressive device further including twisting said first segment and said second segment about one another to draw opposing walls of said left ventricle together.

10. A method for improving cardiac function, comprising:
inserting a tensile member into a patient; and
deploying said tensile member in the patient's heart so as to constrict and close off a lower or apical portion only of only a left ventricle of the patient's heart, thereby reducing the volume of the left ventricle and only the left ventricle of the patient's heart.

11. The method defined in claim 10 wherein the deploying of said tensile member includes anchoring one end of said tensile member to a septum of the patient's heart and an opposite end of said tensile member to a myocardial sidewall of said left ventricle.

12. The method defined in claim 11 wherein the anchoring of said tensile member includes placing a flanged element of said tensile member in contact with heart tissues.

13. The method defined in claim 11 wherein the anchoring of said tensile member includes placing a barbed element of said tensile member in contact with heart tissues.

14. The method defined in claim 10 wherein said tensile member is a tack, the deploying of said tensile member including ejecting said tack from a tubular member.

15. The method defined in claim 10 wherein the deploying of said tensile member includes passing said tensile member through a trocar sleeve or cannula.

16. The method defined in claim 10 wherein the deploying of said tensile member includes:
inserting a leading end portion of a catheter into a vascular system of the patient and into a ventricle of the patient's heart;
ejecting said tensile member from said leading end portion of said catheter into heart tissue so that said tensile member is anchored to the patient's heart tissue; and
exerting tension on said tensile member to pull a septum and a myocardial sidewall of the left ventricle of the patient's heart towards one another so as to constrict and substantially close off only the lower or apical portion of only the patient's left ventricle.

17. The method defined in claim 10 wherein the deploying of said tensile member includes placing sufficient tension on said tensile member in the patient's heart so as to bring opposing inner surface of said left ventricle into substantial contact with one another to thereby effectively constrict and substantially close off the lower or apical portion of the left ventricle of the patient's heart.

18. A method for reducing ventricular volume, comprising:
inserting a leading end portion of a catheter through part of a patient's vascular system and into a ventricle of the patient's heart;
deploying a cardiac insert or implant from said leading end portion of said catheter; and
disposing said cardiac insert or implant in the patient's heart to close off a lower portion of and thereby reduce the volume of only a left ventricle of the patient's heart.

19. The method defined in claim 18 wherein said cardiac insert or implant is a tensile member, further comprising attaching said tensile member to the patient's heart, and exerting tension on said tensile member to draw a septum of the patient's heart and a myocardial sidewall of the patient's left ventricle towards one another at a lower end of the left ventricle.

20. The method defined in claim 19 wherein said tensile member is provided with at least one barb at a leading end, the attaching of said tensile member to the patient's heart including embedding said barb in the patient's heart.

21. The method defined in claim 19 wherein said tensile member is one of two tensile members, further comprising attaching the other tensile member to the patient's heart, the exerting of tension on said one of said tensile members including twisting the tensile members about one another.

\* \* \* \* \*